United States Patent [19]

Golinski et al.

[11] Patent Number: 5,951,969
[45] Date of Patent: Sep. 14, 1999

[54] AGENT FOR THE BRIGHTENING, GLOSS IMPROVEMENT AND DYEING OF HUMAN HAIR

[75] Inventors: Frank Golinski; Frank Kufner, both of Darmstadt; Heribert Lorenz, Gross-Bieberau, all of Germany

[73] Assignee: Goldwell GmbH, Germany

[21] Appl. No.: 08/921,786

[22] Filed: Sep. 2, 1997

[30] Foreign Application Priority Data

Sep. 4, 1996 [DE] Germany ............... 196 35 877

[51] Int. Cl.⁶ .................................................. A61K 7/13
[52] U.S. Cl. ............................................ 424/62; 424/70.1
[58] Field of Search .................................. 424/70.1, 62

[56] References Cited

U.S. PATENT DOCUMENTS

| | | | |
|---|---|---|---|
| 3,962,634 | 6/1976 | Busch | 132/7 |
| 4,840,639 | 6/1989 | Husemeyer et al. | 8/410 |
| 5,161,553 | 11/1992 | Cohen et al. | 132/205 |
| 5,196,029 | 3/1993 | Kawase et al. | 8/405 |
| 5,340,367 | 8/1994 | Schultz et al. | 8/432 |

FOREIGN PATENT DOCUMENTS 62-005836  6/1988  Japan.
406271435  9/1994  Japan.

OTHER PUBLICATIONS

Burns et al., *Chemical Abstracts*, vol. 125, #67158, 1996.
Giede et al., *World Patent Index*, #92–341156, 1992.

*Primary Examiner*—Thurman K. Page
*Assistant Examiner*—Todd Ware
*Attorney, Agent, or Firm*—Londa and Traub LLP

[57] ABSTRACT

The invention concerns a composition for brightening, gloss improvement and, optionally, dyeing of human hair, in particular of permanently waved hair, which contains 0.5 to 12% by weight hydrogen peroxide, and optionally, at least one direct-acting hair dye in an aqueous carrier, having a Brookfield viscosity of 1,000 to 10,000 mPa.s at 25° C.

6 Claims, No Drawings

AGENT FOR THE BRIGHTENING, GLOSS IMPROVEMENT AND DYEING OF HUMAN HAIR

BACKGROUND OF THE INVENTION

The present invention concerns a hair treatment composition, which is preferably used in the final treatment of permanently waved hair, the so-called final fixing, and which has a brightening effect on the hair and improves its gloss.

SUMMARY OF THE INVENTION

In accordance with one of the preferred embodiments, an especially brilliant hair coloring can be achieved by the application of the composition according to the invention.

This composition contains 0.5 to 12% by weight, based on the total composition, of hydrogen peroxide in an aqueous base, and has a viscosity range from 1000 to 10000 mpa.s at 25° C., measured in the Brookfield viscosimeter RVT with spindle no. 4 at 20 rpm.

The preferred viscosity range is about 1500 to 5000 mPa.s at 25° C., in particular 2000 to 4000.

In accordance with a further preferred embodiment of the invention, the composition contains 0.001 to 2.5, especially 0.01 to 1.5, most preferably 0.1 to 1% by weight, based on the total composition, of at least one direct hair dye.

The preferred amount of hydrogen peroxide is from 2 to 8, especially 2.5 to 6% by weight, based on the total composition.

In addition, the invention concerns a process for the brightening, glossing and, optionally, dyeing of permanently waved hair, in which the hair deformed with a reducing agent composition, after the rinsing with water, and optionally after carrying out an intermediate treatment, is fixed as known per se by the application of an oxidation agent composition, and then the composition of the invention is applied, and after about five to about thirty minutes, the hair is rinsed.

By this treatment a glossy brightening of the hair is achieved and, in presence of a direct-acting hair dye, a brilliant hair coloring as well.

Alternatively, the composition in accordance with the invention can also be used for the direct fixing of permanently waved hair or can be applied to the washed or rinsed hair in the course of a hair treatment without a previous permanent wave.

The oxidation agent compositions which are conventionally used for fixing permanently waved hair on the basis of peroxides or alkali bromates have viscosities of less than 1000 mPa.s, usually less than 100 mPa.s, for example between 2.5 and 50 mPa.s, cf. e.g. DE-A 41 31 992; the inventive effect cannot be attained with them.

Without stipulating a special mechanism for the inventive effect, it seems to be possible that by the application of the higher viscosity composition, a more intensive hair contact is effected, which leads to an improved effect. Thereby, the use of additional hair care and conditioning substances in the composition also becomes advantageous.

Suitable thickening agents in the compositions according to the invention are, for example, natural and synthetic polymers, e.g., cellulose derivates such as hydroxyalkyl celluloses, galactoglucomannan polysaccharides such as guar gum and its derivatives, xanthan gum, maltodextrine, acrylic acid homo- and -copolymers, especially of the type "Carbomer", etc., or also the known inorganic thickening agents.

These thickening agents are preferably present in an amount of about 0.1 to about 5% by weight, especially about 0.25 to about 2.5% by weight, based on the total composition; their percentage is of course dependent on the desired viscosity and on the remaining ingredients of the composition.

Preferred cellulose derivates are in particular hydroxyethyl-, hydroxypropyl and hydroxymethyl propyl cellulose; preferred guar derivates are hydroxypropyl guar, i.e. the propylene glycol ether of guar gum, as well as quaternization products thereof, especially hydroxypropyl guar hydroxypropyl trimonium chloride. Other suitable hydroxyalkyl guar derivates are for example hydroxyethyl guar, hydroxybutyl guar and their quaternization products.

Suitable products are on the market under the tradenames "Jaguar HP™", "Jaguar C 17™" and "Jaguar C-162™" as well as "Galactosol™".

If the inventive composition is not an aqueous gel, but on emulsion or dispersion, the viscosity can be adjusted by the ratio emulsifiers/co-emulsifiers, for example non-ionic polyoxyethylene derivatives and fatty alcohols, in the manner known per se.

Fatty acid alkanolamides are also suitable as viscosity increasing compounds.

In principle, as direct hair dyeing substances, all dyes which are admitted for this purpose can be used; attention is drawn in this connection to the German "Verordnung über kosmetische Mittel (Kosmetik-Verordnung)", appendix 3.

Particularly suitable basic (cationic) dyes are:

| | |
|---|---|
| Basic Blue 6, | C.I.-No. 51,175; |
| Basic Blue,7, | C.I.-No. 42,595; |
| Basic Blue 9, | C.I.-No. 52,015; |
| Basic Blue 26, | C.I.-No. 44,045; |
| Basic Blue 41, | C.I.-No. 11,154; |
| Basic Blue 99, | C.I.-No. 56,059; |
| Basic Brown 4, | C.I.-No. 21,010; |
| Basic Brown 16, | C.I.-No. 12,250; |
| Basic Brown 17, | C.I.-No. 12,251; |
| Basic Green 1, | C.I.-No. 42,040; |
| Basic Red 2, | C.I.-No. 50,240; |
| Basic Red 22, | C.I.-No. 11,055; |
| Basic Red 76, | C.I.-No. 12,245; |
| Basic Violet 1, | C.I.-No. 42,535; |
| Basic Violet 3, | C.I.-No. 42,555; |
| Basic Violet 10, | C.I.-No. 45,170; |
| Basic Violet 14, and | C.I.-No. 42,510; |
| Basic Yellow 57, | C.I.-No. 12,719. |

Also the following acidic (anionic) dyes may be used:

| | |
|---|---|
| Acid Black 1, | C.I.-No. 20,470; |
| Acid Blue 9, | C.I.-No. 42,090; |
| Acid Blue 74, | C.I.-No. 73,015; |
| Acid Red 18, | C.I.-No. 16,255; |
| Acid Red 27, | C.I.-No. 16,185; |
| Acid Red 87, | C.I.-No. 45,380; |
| Acid Red 92, | C.I.-No. 45,410; |
| Acid Violet 43, | C.I.-No. 60,730; |
| Acid Yellow 1, | C.I.-No. 10,316; |
| Acid Yellow 23, | C.I.-No. 19,140; |
| Acid Yellow 3, | C.I.-No. 47,005; |
| D&C Brown No. 1, | C.I.-No. 20,170; |
| D&C Green No. 5, | C.I.-No. 61,570; |
| D&C Orange No. 4, | C.I.-No. 15,510; |
| D&C Orange No. 10, | C.I.-No. 45,425:1; |
| D&C Orange No. 11, | C.I.-No. 45,425; |
| D&C Red No. 21, | C.I.-No. 45,380:2; |

-continued

| D&C Red No. 27, | C.I.-No. 45,410:1; |
| D&C Red No. 33, | C.I.-No. 17,200; |
| D&C Yellow No. 7, | C.I.-No. 45,350:1; |
| D&C Yellow No. 8, | C.I.-No. 45,350; |
| FD&C Red No. 4, | C.I.-No. 14,700; |
| FD&C Yellow No. 6, | C.I.-No. 15,985. |

Vegetable dyes can also be used alone or with synthetic direct dyes, for example henna (red or black), alkanna root, laccaic acid (stick lac), logwood powder, madder root, and rhubarb root powder, etc.

The compositions of the invention further contain preferably at least one synthetic or natural hair conditioning polymer, especially in an amount of 0.1 to 2.5, especially 0.25 to 1.5% by weight of the total composition. In principle all kinds of polymers can be used, i.e. nonionic, anionic, amphoteric and cationic polymers, depending on their compatibility with the other ingredients of the composition such as dyes and surfactants.

Suitable cationic polymers are, e.g., the long known quaternary cellulose derivates of the type "Polymer JR", quaternized homo- and co-polymers of dimethyl diallyl ammonium chloride, such as "Merquat$^R$", quaternary vinylpyrrolidone copolymers, especially with dialkyl aminoalkyl (meth)acrylates, such as "Gafquat$^R$", copolymers of vinylpyrrolidone and vinylimidazolinium methochloride, "Luviquat$^R$", polyamino-polyamide derivates, for example copolymers of adipic acid dimethyl amino hydroxy propyl diethylene triamine, such as "Cartaretine$^R$ F", and bis-quaternary long-chain ammonium compounds of the urea structure which are described in U.S. Pat. No. 4,157,388 and which are on the market under the trademark "Mirapol$^R$ A 15".

Attention is drawn also to the cationic polymers described in DE-A 25 21 960, DE-A 28 11 010, DE-A 30 44 738 and DE-A 32 17 059, as well as to the products which are disclosed in EP-A 0 337 354 on pages 3 to 7. Mixtures of different cationic polymers can also be used.

Instead of cationic polymers or in combination with them, nonionic polymers are also suitable. Such nonionic polymers, vinyl pyrrolidone homo- and copolymers, especially polyvinyl pyrrolidone itself, copolymers of vinyl pyrrolidone and vinyl acetate or terpolymerisates of vinyl pyrrolidone vinyl acetate and vinyl propionate such as are sold by the under the tradename "Luviskol$^R$".

(Co-)polymers of the various acryl and methacryl esters, acrylamide and methacrylamide can also be used, for example polyacrylamide with molecular weights of more than 100,000, dimethylhydantoin-formaldehyde resins, etc. Of course, mixtures of various nonionic polymers are also appropriate.

Suitable anionic polymers within the framework of the invention are vinyl alkyl ether polymers, especially methyl vinyl ether/maleic acid copolymers, which are formed by hydrolysis of vinyl ether/maleic anhydride copolymers and are sold under the tradenames "Gantrez$^R$ AN or ES". These polymers can also be partly esterified, for example "Gantrez$^R$ ES 225", being the ethyl ester of an ethyl vinyl ether/maleic acid copolymer or the butyl- or isobutyl ester thereof.

Other suitable anionic polymers are in particular vinyl acetate crotonic acid or vinyl acetate/vinyl neodecanoate/crotonic acid copolymers of the type "Resy$^R$"; sodium acrylate/vinyl alcohol copolymers of the type "Hydagen$^R$ F", sodium polystyrene sulfonate, e.g. "Flexan$^R$ 130; ethyl acrylate/acrylic acid/N-tert.-butylacrylamide copolymers of the type "Ultrahold$^R$"; vinyl pyrrolidone/vinyl acetate/itaconic acid copolymers, acrylic acid/acrylamide copolymers and/or the sodium salts thereof of the type "Reten$^R$", etc.

In principle, all the anionic polymers which have been suggested for use in hair care agents can be used, provided they are compatible with the other components of the inventive composition.

Amphoteric polymers, which are used either alternatively or in the admixture with others, especially cationic polymers, include copolymers of N-octyl acrylamide, (meth)acrylic acid and N-tert butyl aminoethyl methacrylate of the type "Amphomer$^R$"; copolymers of methacryloylethyl betaine and alkyl methacrylates of the type "Yukaformer$^R$", e.g. the butyl methacrylate copolymer "Yukaformer$^R$ AM75"; copolymers containing carboxylic groups or sulfo groups, e.g. (meth)acrylic acid and itaconic acid copolymers, with basic monomers containing amino groups such as mono- and dialkyl aminoalkyl (meth)acrylates and/or mono- and dialkyl aminoalkyl (meth)acrylamides; copolymers of N-octylacryl amide, methacrylates, hydroxypropyl methacrylate, N-tert.butyl aminoethyl methacrylate and acrylic acid as well as the copolymers which are known from U.S. Pat. No. 3,927,199.

The inventive hair gloss compositions may contain additives which are conventional in such compositions, the type and character of which depend on the application form of the compositions.

These are surfactants, especially anionics such as alkyl (ether) sulfates, polyether carboxylic acids, alkyl amidoether carboxylic acids, long- chain N-acylamino carboxylic acids and their salts such as N-lauroyl sarcosinate and glutamate, amphoterics such as betaines, e.g. cocoamidopropyl betaine as well as nonionics and cationics, fats, fatty alcohols, emulsifiers, pH-regulators, solvents and binding agents, solubilizers, preservatives, perfumes, etc.

The pH-value of the compositions in accordance with the invention is preferably in the range from 3 to 7, preferably 4 to 6.

DETAILED DESCRIPTION OF THE INVENTION

The following Examples illustrate the invention and its effects in detail.

A basic formula of the following Composition I was prepared:

| | |
|---|---|
| Cetylstearyl alcohol | 3.0(%byweight) |
| Sodium cetylstearyl sulfate | 0.3 |
| Stearic acid monoethanolamide | 0.5 |
| Coconut fatty acid monoethanolamide | 0.6 |
| Coconut fatty acid monoethanolamide, ethoxylated with 4 moles EO | 0.2 |
| Hydroxyethyl cellulose | 0.2 |
| Sodium lauryl sulfate | 0.2 |
| Chelating agent | 0.1 |
| Ammonium chloride | 0.1 |
| Ascorbic acid | 0.1 |
| Horse chestnut extract | 0.2 |
| Wheat protein hydrolyzate | 0.2 |
| Perfume | 0.2 |
| Hydrogen peroxide | 4.0 |

| Water | @100.0 |
| --- | --- |
| pH-value: 4.5 | |
| Viscosity at 25° C.: 2000 mPa.s | |
| (measured in a Brookfield viscosimeter RVT with spindle no. 4 at 20 rpm.) | |

EXAMPLE 1

Composition I was applied on a moistened dark-brown strand of human hair and was rinsed out and dried after 30 minutes.

The strands showed a medium brown gloss.

In a comparative test, an identical strand of hair was treated with an identical composition, which did not contain any hydroxyethyl cellulose and only had a viscosity of 250 mPa.s at 25° C.

The appearance of the strands was unchanged after the treatment.

EXAMPLE 2

Composition I, which contained in addition 0.1% by weight of the direct hair dye Disperse Violet 4 (with removal of 0.1% by weight of water), was applied in the half-side test to one half of permanently waved hair having a greyish color which had been pre-fixed with a conventional 6% hydrogen peroxide solution.

The other half was treated with an identical composition, whose viscosity however had been adjusted to 100 mPa.s at 25° C.

After 15 minutes, rinsing and drying results were compared on both halves.

The half of the hair which was treated with the inventive composition showed a glossy silver coloring, whereas the comparison composition led to a grey color showing no lustre.

EXAMPLE 3

A mixture of direct hair dyes was added to Composition I, with a corresponding reduction of the share of water:

| Basic Blue 99 | 0.01 (% by weight) |
| --- | --- |
| Basic Brown 16 | 0.02 |
| Basic Brown 17 | 0.03 |
| Basic Yellow 57 | 0.04 |

This composition was applied in the half-side test to moist, medium blonde hair; an identical composition with a viscosity adjusted to <100 mPa.s at 25° C. was applied to the other half of this hair.

After 15 minutes, the hair was rinsed, dried and the appearance of the two halves of the hair was compared.

Whereas the half of the hair treated with the inventive Composition I had a bright and glossy, gold-yellow coloring, the half with the comparison composition showed a dull blond tone.

EXAMPLE 4

In a further half-side test, one half of the hair of a test person with medium brown hair was treated with Composition I, which contained the following combination of direct hair dyes:

| Basic Blue 99 | 0.12 (% by weight) |
| --- | --- |
| Basic Brown 16 | 0.17 |
| Basic Brown 17 | 0.07 |
| HC Yellow 5 | 0.12 |
| HC Red 3 | 0.20 |
| (weight-balanced by reduction of the water content). | |

The other hair half was treated with an identical composition which, however, had a reduced viscosity of 100 mPa.s at 25° C. The comparison of the two halves of the hair showed after 20 minutes of treatment and subsequent rinsing and drying for the hair half treated with the inventive composition a glossy, strong red-brown coloring, whereas the hair-half treated with the low viscosity composition only had a dull, reddish-brown color tone.

EXAMPLE 5

A Composition II was prepared containing:

| Hydrogen peroxide | 2.2 | (%byweight) |
| --- | --- | --- |
| Hydroxypropyl trimonium guar | 1.2 | |
| Polyethylene glycol 10 000 | 6.0 | |
| Polypropylene glycol-30/ polyethylene glycol-150 | 1.0 | |
| Wheat protein hydrolysate | 0.3 | |
| Potassium sorbate | 0.1 | |
| Water | @100.0 | |
| Viscosity at 25° C. (Brookfield RVT, spindle 4 at 20 rpm): 3500 mPa.s | | |
| pH-value: 6.8 | | |

This composition was applied on a moistened strand of medium brown human hair, which was rinsed and dried after 20 minutes of treatment.

A glossy light brown color was obtained; the hair had good combability, volume and resilience.

An identical composition, which only had a viscosity of 10 mPa.s at 25° C. by the omission of the thickening agent, effected after the same treatment in an unchanged dull brown color, the combability, volume and elasticity were significantly lower than that of the strands treated with the inventive compisition.

EXAMPLE 6

In a further half-side test the medium blonde hair of a test subject was divided into two halves, curled, subjected to a normal permanent wave treatment, and rinsed.

One half was treated with a fixing agent of Composition III comprising:

| Hydrogen peroxide | 2.6 | (%byweight) |
| --- | --- | --- |
| Disodium hydrogen phosphate | 0.2 | |
| Polyquaternium-10 | 0.3 | |
| Ethylene oxide/propylene oxide condensate | 0.5 | |
| Hydrogenated polyethyleneglycol-10 Castor Oil | 0.2 | |
| Perfume | 0.2 | |
| Distearyl dimethyl ammonium chloride | 0.4 | |
| Hydroxypropylmethyl cellulose | 1.5 | |
| Water | @100.0 | |

-continued

| | |
|---|---|
| Phosphoric acid for adjustment to | pH3.5 |
| Viscosity at 25° C. (Brookfield RVT, spindle 4 at 20 rpm): | |
| 2300 mPa.s | |

The other half was treated with an identical composition, the viscosity of which, however, was only 150 mpa.s at 25° C. After 10 minutes and subsequent rinsing the curlers were removed, and the hair was dried.

The hair half fixed with the inventive composition showed a bright gloss and better combability and was more flexible and fluffier than the hair which was fixed with the low-viscous composition.

We claim:

1. A process for the treatment of permanently waved hair, comprising the steps of
    deforming hair with a reducing agent composition,
    rinsing with water,
    optionally providing an intermediate treatment,
    fixing by the application of an oxidizing composition,
    applying to the hair a composition according to claim 1, and
    rinsing out after a treatment of 5 to 30 minutes.

2. A process for the brightening and gloss improvement of human hair, comprising
    applying onto the hair a composition for the brightening and gloss improvement of human hair, said composition comprising 0.5 to 12% by weight hydrogen perixode, based on the total composition, in an aqueous carrier, having a viscosity of 1,000 to 10,000 mPa.s at 25° C. (measured in a Brookfield viscosimeter RVT with spindle No. 4 at 20 rpm) and
    rinsing out the composition after 5 to 30 minutes' treatment,
    so as to achieve a brightening and gloss improvement to the hair.

3. The process for the brightening and gloss improvement of human hair according to claim 2, wherein the viscosity is from 1,500 to 5,000 mpa.s at 25° C.

4. The process for the brightening and gloss improvement of human hair according to claim 2, further comprising at least one direct-acting hair dye.

5. The process for the brightening and gloss improvement of human hair according to claim 2, wherein the at least one direct-acting hair dye is present in an amount 0.001 to 2.5% by weight, based on the total composition.

6. The process for the brightening and gloss improvement of human hair according to claim 2, having a pH-value of 3 to 7.

* * * * *

UNITED STATES PATENT AND TRADEMARK OFFICE
CERTIFICATE OF CORRECTION

PATENT NO. : 5,951,969

DATED : September 14, 1999

INVENTOR(S) : Frank Golinski; Frank Kufner and Heribert Lorenz

It is certified that an error appears in the above-identified patent and that said Letters Patent is hereby corrected as shown below:

In column 7, line 23, cancel "according to claim 1" and insert --containing 0.5 to 12% by weight hydrogen peroxide, based on the total composition, in an aqueous carrier, wherein it has a viscosity of 1,000 to 10,00 mPa.s at 25°C (measured in a Brookfield viscosimeter RVT with spindle No. 4 at 20 rpm).

Signed and Sealed this

Nineteenth Day of September, 2000

Attest:

Q. TODD DICKINSON

*Attesting Officer*  *Director of Patents and Trademarks*